United States Patent

Chakrabarti et al.

[11] 4,061,774
[45] Dec. 6, 1977

[54] HALOGENATED AMINO METHYL ADAMANTANE DERIVATIVES

[75] Inventors: Jiban Kumar Chakrabarti, Camberley; Terrence Michael Hotten, Farnborough; David Edward Tupper, Bracknell, all of England

[73] Assignee: Lilly Industries, Limited, London, England

[21] Appl. No.: 566,502

[22] Filed: Apr. 9, 1975

Related U.S. Application Data

[63] Continuation-in-part of Ser. No. 554,023, Feb. 28, 1975, abandoned.

[30] Foreign Application Priority Data

Mar. 2, 1974 United Kingdom ............... 9521/74
Mar. 4, 1974 United Kingdom ............... 9576/74

[51] Int. Cl.² .................. A61K 31/13; C07C 87/40
[52] U.S. Cl. .................. 424/325; 260/268 PC; 260/293.56; 260/326.8; 260/631 R; 260/348.11; 260/563 P; 424/248.4; 424/250; 424/267; 424/274; 544/154
[58] Field of Search ...... 260/563 R, 268 BF, 268 PC; 424/250, 325

[56] References Cited

U.S. PATENT DOCUMENTS 3,859,352  1/1975  Szinai et al. ............... 260/563 P

OTHER PUBLICATIONS

Tabushi et al., Chemical Abstracts, vol. 68 (1968), abstract 86,625w, p. 8333.
E. I. Du Pont de Nemours & Co., Chemical Abstracts, vol. 63, p. 516c (1965).
E. I. Du Pont de Nemours & Co., Chemical Abstracts, vol. 75, p. 140372w, (1971).

Primary Examiner—Donald G. Daus
Assistant Examiner—David E. Wheeler
Attorney, Agent, or Firm—Kathleen R. S. Page; Everet F. Smith

[57] ABSTRACT

Novel 2-substituted-1-methylamino adamantanes of formula:

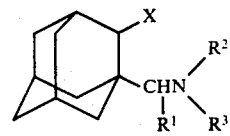

where X is hydroxyl or halogeno, and $R^1$, $R^2$ and $R^3$ are hydrogen or $C_{1-4}$ alkyl or $R^2$ and $R^3$ together with the nitrogen form a heterocyclic ring, having anti-Parkinsonian activity, pharmaceutical formulations containing the active adamantanes and novel 4-protoadamantane spiro oxirane and 1,2-difunctionalized intermediates useful in the preparation of the final products of the invention.

12 Claims, No Drawings

HALOGENATED AMINO METHYL ADAMANTANE DERIVATIVES

CROSS-REFERENCE

This application is a continuation-in-part of our co-pending Application Ser. No. 554,023, filed Feb. 28th 1975, now abandoned.

This invention relates to novel adamantane derivatives having useful pharmacological activity, to pharmaceutical formulations containing the novel adamantanes, to novel intermediates and processes for preparing the novel compounds of the invention.

Many substituted adamantanes have been shown to be useful as oil additives, agricultural chemicals and pharmaceuticals but a study of the literature reveals that the majority of such compounds are substituted exclusively at the bridge-hand positions. Where 1,2-disubstituted adamantanes have been made, their synthesis has required a multi-stage, time consuming process from available mono-substituted adamantanes such as 1-hydroxyadamantane and necessarily the types of substituent introducible at the 1- and 2-positions by such methods are limited. There is therefore a need to provide a means of functionalising adamantane in the 1- and 2-positions so as to permit subsequent reactions to be carried out at these positions without the problems associated with the prior art processes.

According to one aspect of the present invention therefore, there are provided 1,2-difunctionalised adamantanes of the formula:

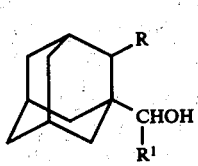

where R is hydroxyl or halogeno, especially chloro or bromo, and $R^1$ is hydrogen, or $C_{1-4}$ alkyl.

Preferably $R^1$ is hydrogen. The compounds of formula I are therefore 2-hydroxy- or 2-halogeno-1-adamantane methanols which, as well be appreciated by those skilled in the art, are particularly suitable as intermediates capable of participating in a wide variety of chemical reactions due to the presence in the molecule at the 1- and 2-positions of either two hydroxyl functions or a hydroxyl and halogeno function.

For instance, the hydroxy compounds of formula I where R is halo may be converted to the amino derivatives of formula III, described hereinafter, simply by converting the —CHOH group to a —CHOTs group, where Ts is tosyl, followed by a condensation reaction with the appropriate amine. Similarly, compounds of formula I, where R is hydroxyl, may be converted to dihalo derivatives using a halogenating agent such as thionyl bromide. The dihalo compound is then reacted with the appropriate amine whereupon selective displacement of the halogen atom in the $CH_2X$ substituent at the 1-position occurs. Both the tosylation reaction and halogenation, and the subsequent condensation with the amine are well-known reactions which would present no problem to one skilled in the art.

The present invention also provides a process by which the compounds of formula I can be prepared characterised by acid re-arrangement of the appropriate 4-protoadamantane spiro oxirane of the formula:

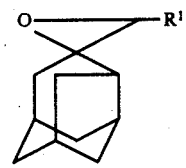

where $R^1$ is as defined above. In the case where R in the desired compound of formula I is halogeno, the re-arrangement is carried out under anhydrous conditions by treatment of the spiro oxirane of formula II with the appropriate hydrogen halide. When R represents hydroxyl in the compound of formula I, the re-arrangement is accomplished using an aqueous solution of an inorganic acid, preferably dilute sulphuric acid.

The compounds of formula II are themselves novel and form a part of this invention. Compounds of formula II in which $R^1$ is hydrogen are particularly preferred. They are prepared from 4-protoadamantanone(-tricyclo[4,3,2,0$^{3,8}$]decan-4-one) either by reaction with trimethyl sulphonium iodide or trimethylsulphoxonium iodide where $R^1$ is hydrogen, or by reaction at low temperature with the appropriate alkylidene or benzylidene halide in the presence of lithium metal or an alkyl lithium compound where $R^1$ is $C_{1-4}$ alkyl. If desired, the resultant spiro oxirane may be re-arranged in situ to the desired product of formula I.

4-Protoadamantanone is a known compound which is readily prepared from 1-hydroxyadamantane, for example by the method described in the Journal of the Chemical Society (C), 2124 (1970).

The oxiranes of formula II can be converted to pharmacologically-active compounds of the formula:

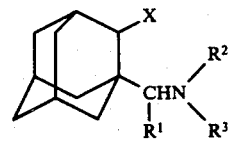

wherein X represents a halogen atom, $R^1$ is as defined above and $R^2$ and $R^3$ independently represent hydrogen or $C_{1-4}$ alkyl or together with the adjacent nitrogen represent a heterocyclic ring, via the intermediates of formula IV described hereinbelow.

Accordingly in a second aspect of the present invention, there is provided a compound of formula III:

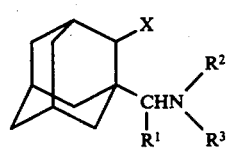

wherein X represents a halogen atom, preferably a bromine or chlorine atom; $R^1$ is hydrogen or $C_{1-4}$ alkyl, and wherein $R^2$ and $R^3$ are the same or different and represent hydrogen, a $C_{1-4}$ alkyl group or taken together with the nitrogen atom form a mononuclear heterocyclic ring system having between 4 and 6 carbon atoms and not more than two heteroatoms such as N-phenyl or N-$C_{1-4}$ alkylpiperazino, for example N-methylpiperazino, morpholino, piperidino or pyrrolidino; or an acid addition salt thereof.

Compounds in which $R^1$ is hydrogen are preferred.

When $R^2$ and $R^3$ taken together represent a heterocyclic ring, it is preferred that the heterocyclic ring is an N-phenyl or N-$C_{1-4}$alkylpiperazino group.

The acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, malic, tartaric, citric, salicyclic, o-acetoxybenzoic, nicotinic or isonicotinic acid, or organic sulphonic acids for example methane sulphonic, ethane sulphonic, 2-hydroxyethane sulphonic, toluene-p-sulphonic, or naphthalene-2-sulphonic acid. Apart from pharmaceutically acceptable acid addition salts, other salts are also included within the scope of acid addition salts such as, for example, those with picric or oxalic acid; they may serve as intermediates in the purification of the compounds or in the preparation of other, for example, pharmaceutically acceptable, acid addition salts, or are useful for identification, characterization or purification of the bases.

A resulting acid addition salt may be converted into the free compound according to known methods, for example, by treating it with a base, such as with a metal hydroxide or alkoxide, for example an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example, sodium, potassium or calcium carbonate or hydrogen carbonate; with ammonia; or with a hydroxyl ion exchange preparation, or with any other suitable reagent.

The presently preferred compounds of the invention are those of formula III wherein X represents a bromine atom, $R^1$ represents a hydrogen atom and where $R^2$ represents hydrogen and $R^3$ represents a methyl group, or wherein $R^2$ and $R^3$ taken together with the nitrogen atom represent N-methylpiperazino.

The preferred acid addition salts are the hydrochloride and the hydrobromide.

The compounds of formula III possess significant anti-Parkinsonian activity and hence are useful in the relief of Parkinsonism. The usefulness of these compounds has been demonstrated in well-known test procedures such as antagonism of reserpine hypothermia in mice and reserpine catalepsy in rats.

According to a third aspect of the invention, there is provided a method of preparing a compound of formula III which comprises reacting a compound of formula IV:

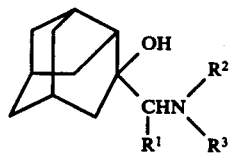

IV with HX, preferably hydrogen bromide or chloride, optionally in the presence of a suitable inert solvent.

Of course, compounds where one or both of $R^2$ and $R^3$ represent a hydrogen atom can easily be converted into the corresponding N-alkyl derivatives by standard alkylation techniques known in the art.

The intermediates of formula IV are themselves novel compounds and are accordingly provided in a further aspect of the invention. Intermediates of formula IV in which $R^1$ is hydrogen are preferred.

The compounds of formula IV can be derived from the oxiranes of structure II by reaction with the appropriate primary or secondary amine of formula $R^2R^3NH$. For example, the oxirane of formula:

V can be reacted with the primary or secondary amine of formula $R^2R^3NH$ to yield a compound of formula IV in which $R^1$ is hydrogen. A suitable alkanol solvent such as ethanol can be utilised to carry out the reaction. If desired, the reaction mixture may be refluxed, or heated in a sealed vessel.

According to yet a further aspect of the invention, there is provided a pharmaceutical formulation containing as an active ingredient a compound of formula III or a pharmaceutically-acceptable addition salt thereof, in association with at least one pharmaceutically-acceptable carrier therefor.

As noted above, the compounds of the present invention form acid addition salts and, where such salts are pharmaceutically-acceptable they are equally useful for the treatments mentioned previously. The compounds and the pharmaceutically-acceptable acid addition salts thereof of this invention are effective over a wide dosage range, the actual dose administered being dependent on such factors as the particular compound being used, the condition being treated and the type and size of mammal being treated. However, the dosage required will normally fall within the range of 0.1 to 100 mg./Kg. per day, for example in the treatment of adult humans dosages of from 0.5 to 15 mg,/Kg. may be used whilst, in the treatment of test animals such as mice and rats, dosages of from 5 to 75 mg./Kg. may be employed.

The compounds and salts of the present invention will normally be administered orally or by injection and, for this purpose, said compounds and salts will usually be utilised in the form of a pharmaceutical composition. Such compositions are prepared in a manner well known in the pharmaceutical art and normally comprise at least one active compound or salt of the invention in association with a pharmaceutically acceptable carrier therefor. In making the composition of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-soid or liquid material which acts as a vehicle, excipient or medium for the active ingredient. Some examples of of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc, magnesium stearate or mineral oil. The compositions of the invention may, as is well known in the art, be formulated so as to provide quick, sustained or delayed release of the active ingredient after administration to the patient.

Depending on the route of administration, the foregoing compositions may be formulated as tablets, capsules or suspensions for oral use and injection solutions for parenteral use. Preferably the compositions are formulated in a dosage unit form, each dosage containing from 1 to 500 mg., more usually 5to 250 mg., of the active ingredient.

The following Examples illustrate the invention

EXAMPLE 1

4-Protoadamantane spiro oxirane

A 500 ml., three necked round-bottomed flask was fitted with oil bath, mechanical stirrer and nitrogen inlet. The nitrogen outlet was connected to an empty Dreschel bottle and then to a tap containing chromic acid (to destroy dimethyl sulphide formed in the reaction).

4-Protoadamantanone (15.1 g., 0.1 mole) and trimethyl sulphonium iodide (31 g., 0.15 mole) were placed in the flask and dry dimethyl sulphoxide (200 ml.) added. The mixture was stirred until all solid was dissolved and solid potassium tert. butoxide (14 g.) was added in one portion.

The mixture was warmed to 50° – 55° C., maintained at that temperature for 18 hours, cooled to 10° C. in an ice-bath and ice-water (200 ml.) added. After extraction with carbon tetrachloride (3 × 100 ml.), the combined extracts were washed with water (3 × 100 ml.), dried over $MgSO_4$ and evaporated to dryness under vacuum to give an oil, ca. 16.3 g. The oil was distilled at 70° – 80° C.1.3 mm. Hg. Yield 12.8 g. (78%).

A sample was further purified by sublimation at 50° C./0.7 mm. Hg., to give a white waxy solid, m.p. 62° – 64° C. Ir, $\nu_{MAX}$ 3020, 2960 – 2840 cm.$^{-1}$. 1255, 1270, 1290 cm.$^{-1}$.

Analysis: Calculated: C, 80.43; H, 9.82; O, 9.74; Found: C, 80.29; H, 9.68; O, 10.01

EXAMPLE 2

2-Hydroxy-1-adamantane methanol

4-Protoadamantane spiro oxirane (7.0 g., 0.043 mole) was dissolved in dioxan (150 ml.) and water (20 ml.). To the solution was added 10% $H_2SO_4$ (2ml.) and the mixture left at room temperature overnight. The dioxan was removed slowly under vacuum at ~50° C. and water added to the residue simultaneously until crystallisation of the product was complete. The resulting white solid was filtered and dried at 50° C. under vacuum. Yield 7.3 g. of 2-hydroxy-1-adamantane methanol, m.p. 172° – 174° C. after re-crystallisation from di-isopropylether-hexane.

Analysis: Calculated: C, 72,48; H, 9.95; O, 17.55; Found C, 72,38; H, 10.21; O, 17.73.

EXAMPLE 3

2-Bromo-1-adamantane methanol

4-Protoadamantane spiro oxirane (5 g., 0.03 M) in a little dry dioxan was added to a saturated solution of hydrogen bromide in dioxan (40 ml.) at 10° C. The solution was stirred at 10° C. for 30 minutes and then at 25° C. for 20 hours. The solvent was evaporated and the residue re-crystallised from n-hexane to yield the desired product, 2.62 g (35%) m.p. 138° C (sublimes).

Analysis $C_{11}H_{17}BrO$ Calculated: C, 53.89; H, 6.9; Br 32.59; O, 6.53; Found: C, 54.17; H, 7.11; Br 32.38;O, 6.81%.

EXAMPLE 4

4-N-Methylaminomethylprotoadamantan-4-ol maleate

Protoadamantane-4-spiro oxirane (10.0 g., 0.06 mole) was stirred in a sealed vessel with 33% methylamine in ethanol (50 ml.) for 20 hours at 50° C This was evaporated to an oil, dissolved in ethanol (100 ml.) and then maleic acid (8 g., 0.07 mole) was added. Ether was added to the refluxing solution until crystallisation began. Crystals were filtered off and dried in vacuo at 60° C. The yield was 11.65 g. (61%), m.p. 160° – 162° C.

Analysis: $C_{16}H_{25}NO_5$ C: 61.72; H: 8.09; N: 4.50; O:25.69%; Found: C: 61.53; H: 8.23; N: 4.32; O: 25.78%.

EXAMPLE 5

4-N,N-Dimethylaminomethylprotoadamanatan-4-ol hydrochloride

The above-identified compound was prepared by a similar procedure to that of Example 4. The yield was 48% and the melting point of the hydrochloride was 250° C.

Analysis: $C_{13}H_{24}ClNO.^1/3H_2O$; Required: C: 62.01; H: 9.87; N: 5.56; Cl: 14.08%; Found: C: 61.86; H: 9.50; N: 5.51; Cl: 14.05%.

EXAMPLE 6

2-Bromo-1-N-methylaminomethyladamantane hydrochloride

4-N-Methylaminomethyl protoadamantan-4-ol (1.6 g., 0.008 mole) was dissolved in absolute ethanol (15 ml.) and anhydrous HBr passed into the solution for 15 minutes. The dissolution of HBr in the ethanol caused the solution to reflux. The mixture was left for 2 days and then evaporated in vacuo to give a yellow solid (2.8 g.). This yellow solid was dissolved in water and basified with 2N.NaOH. Extraction with $CCl_4$ was then carried out and the free base chromatographed on basic alumina (activity grade 1) by elution with chloroform, to remove any 2-hydroxy compound present. The pure 2-bromo amine was converted to its hydrochloride and re-crystallised from I.P.A./hexane. The yield was 0.6 g. (25%), m.p. 269° – 272° C.

Analysis: $C_{12}H_{21}BrClN$; Required: C: 48.91; H: 7.18; N: 4.75%; Found: C: 49.13; H: 6.90;N: 4.85%.

EXAMPLE 7

2-Bromo-N,N-dimethylaminomethyladamantane hydrochloride

The above-identified compound was prepared by a similar procedure to that described in Example 6. The yield was 36% and the melting point of the hydrochloride was 185° C.

Analysis: $C_{13}H_{23}BrClN\frac{1}{2}H_2O$; Required: C: 49.14; H: 7.61; N: 4.41%; Found: C: 49.14; H: 7.68; N: 4.35%.

EXAMPLE 8

4-(4-Methyl-1-piperazinyl)methylprotoadamantan-4-ol dihydrochloride

To a solution of 4-protoadamantane spiro oxirane (1.64 g., 0.01 mole) in ethanol (40 ml.) was added 4-methylpiperazine (5g., 0.05 mole). The solution was heated under reflux for 18 hours. The mixture, when cold, was diluted with water and extracted with $CH_2Cl_2$. The organic phase was washed several times with water, dried ($MgSO_4$) and evaporated under vacuum to an oil, ca. 2.5 g. The base was then converted to hydrochloride which was crystallised from methanol, ca. 1.8 g., m.p. 232° – 234° C.

Analysis: $C_{16}H_{28}N_2 0.2HCl$; Required: C: 56.96; H: 8,97; N: 8.29; Cl: 21.01%; Found: C: 56.68; H: 9.15; N: 8.01; Cl: 20.82%.

EXAMPLE 9

2-Bromo-1-(4-methyl-1-piperazinyl)methyladamantane dihydrobromide 4-(4-Methyl-1-piperazinyl) methylprotoadamantan-4-ol (1.3 g., 0.005 mole) was treated with 45% HBr in acetic acid (10 ml.). The mixture was stirred for 24 hours at room temperature, evaporated in vacuo at 40° – 50° C. The white solid (1 g.) so formed was crystallised from ethanol, m.p. 246° – 249° C. (dec.).

Analysis: $C_{16}H_{27}BrN_2$; 2HBr Required: C: 39.29; H: 5.98; N: 5.73%; Found: C: 39.46; H: 5.81; N: 5.74%.

We claim:
1. A compound of the formula

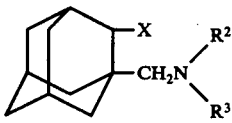

wherein X represents a halogen atom, and wherein $R^2$ and $R^3$ are the same or different and represent hydrogen or a $C_{1-4}$ alkyl group, at least one of $R^2$ and $R^3$ being $C_{1-4}$ alkyl; or a pharmaceutically acceptable non-toxic acid addition salt thereof.

2. A compound according to claim 1, wherein X is bromine or chlorine.

3. A compound according to claim 1, wherein both of $R^2$ and $R^3$ represent $C_{1-4}$ alkyl groups.

4. A compound according to claim 1, wherein X is bromine or chlorine and wherein at least one of $R^2$ and $R^3$ is methyl.

5. The compound of claim 1 which is 2-bromo-1-N-methylaminomethyladamantane hydrochloride.

6. The compound of claim 1 which is 2-bromo-1-N,N-dimethylaminomethyladamantane hydrochloride.

7. A pharmaceutical formulation containing as an active ingredient into anti-Parkinsonian effective amount of a compound of claim 1 associated with a pharmaceutically acceptable carrier therefor.

8. The formulation of claim 7 wherein the adamantane compound is 2-bromo-1-N-methylaminomethyladamantane hydrochloride.

9. The formulation of claim 7 wherein the adamantane compound is 2-bromo-1-N,N-dimethylaminomethyladamantane hydrochloride.

10. A method of treating a human suffering from Parkinson's disease which comprises administering a therapeutically effective amount of an adamantane compound of claim 1 to the human.

11. The method of claim 10 wherein the adamantane compound is 2-bromo-1-N-methylaminomethyladamantane hydrochloride.

12. The method of claim 10 wherein the adamantane compound is 2-bromo-1-N,N-dimethylaminomethyladamantane hydrochloride.

* * * * *